US00PP30615P3

(12) United States Plant Patent
Palmer et al.

(10) Patent No.: US PP30,615 P3
(45) Date of Patent: Jun. 25, 2019

(54) ***ARGYRANTHEMUM* PLANT NAMED 'G15101'**

(50) Latin Name: *Argyranthemum frutescens*
Varietal Denomination: G15101

(71) Applicants: Irene E. Palmer, Mills River, NC (US); Michael S. Owen, Cascade, MT (US)

(72) Inventors: Irene E. Palmer, Mills River, NC (US); Michael S. Owen, Cascade, MT (US)

(73) Assignee: GardenGenetics LLC, Bellafonte, PA (US)

( * ) Notice: Subject to any disclaimer, the term of this patent is extended or adjusted under 35 U.S.C. 154(b) by 53 days.

(21) Appl. No.: 15/732,081

(22) Filed: Sep. 14, 2017

(65) Prior Publication Data

US 2019/0082580 P1 Mar. 14, 2019

(51) Int. Cl.
*A01H 5/02* (2018.01)
*A01H 6/14* (2018.01)

(52) U.S. Cl.
USPC ..... Plt./406
CPC ..... *A01H 6/14* (2018.05)

(58) Field of Classification Search
USPC ..... Plt./406
See application file for complete search history.

*Primary Examiner* — Anne Marie Grunberg
(74) *Attorney, Agent, or Firm* — C. A. Whealy

(57) ABSTRACT

A new and distinct cultivar of *Argyranthemum* plant named 'G15101', characterized by its upright and somewhat outwardly spreading plant habit; freely branching habit; dense and bushy appearance; freely flowering habit; large single-type inflorescences with dark yellow-colored ray florets and yellow orange-colored disc florets; and good garden performance.

1 Drawing Sheet

Botanical designation: *Argyranthemum frutescens*.
Cultivar denomination: 'G15101'.

CROSS-REFERENCED TO CLOSELY-RELATED APPLICATIONS

Title: *Argyranthemum* Plant Named 'G15104'
Applicants: Irene E. Palmer & Michael S. Uchneat
Filed: Concurrently with this application, having U.S. Plant Pat. No. 29,843

BACKGROUND OF THE INVENTION

The present invention relates to a new and distinct cultivar of *Argyranthemum* plant, botanically known as *Argyranthemum frutescens* and hereinafter referred to by the cultivar name 'G15101'.

The objective of the breeding program is to create new *Argyranthemum* plants with attractive ray and disc floret colors, sterility and good garden performance.

The new *Argyranthemum* plant is a naturally-occurring whole plant mutation of *Argyranthemum frutescens* 'Butterfly', not patented. The new *Argyranthemum* plant was discovered and selected by the Inventors as a single flowering plant from within a population of plants of 'Butterfly' in a controlled greenhouse environment in Bellefonte, Pa. in October, 2014.

Asexual reproduction of the new *Argyranthemum* plant by vegetative tip cuttings was first conducted in Bellefonte, Pa. on Nov. 17, 2014. Asexual reproduction by terminal vegetative cuttings has shown that the unique features of this new *Argyranthemum* plant are stable and reproduced true to type in successive generations.

SUMMARY OF THE INVENTION

Plants of the new *Argyranthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of the new *Argyranthemum* plant. These characteristics in combination distinguish 'G15101' as a new and distinct *Argyranthemum* plant:

1. Upright and somewhat outwardly spreading plant habit.
2. Freely branching habit; dense and bushy appearance.
3. Freely flowering habit.
4. Large single-type inflorescences with dark yellow-colored ray florets and yellow orange-colored disc florets.
5. Good garden performance.

Plants of the new *Argyranthemum* differ from plants of the mutation parent, 'Butterfly', in ray floret color as ray florets of the new *Argyranthemum* are darker yellow in color than ray florets of plants of 'Butterfly'.

Plants of the new *Argyranthemum* differ from plants of *Argyranthemum frutescens* 'G15104', disclosed in a U.S. Plant Patent application filed concurrently, in the following characteristics:

1. Plants of the new *Argyranthemum* have larger inflorescences than plants of 'G15104'.
2. Ray florets of the new *Argyranthemum* are darker yellow in color than ray florets of plants of 'G15104'.

Plants of the new *Argyranthemum* can be compared to plants of *Argyranthemum frutescens* 'Vanilla', disclosed in U.S. Plant Pat. No. 14,642. In side-by-side comparisons, plants of the new *Argyranthemum* differ primarily from plants of 'Vanilla' in the following characteristics:

1. Plants of the new *Argyranthemum* have larger ray florets than plants of 'Vanilla'.
2. Ray florets of the new *Argyranthemum* are dark yellow in color whereas ray florets of plants of 'Vanilla' are initially yellow in color and become creamy white in color with development.

Plants of the new *Argyranthemum* can also be compared to plants of *Argyranthemum frutescens* 'Butterfly Yellow', not patented. In side-by-side comparisons, plants of the new *Argyranthemum* differ primarily from plants of 'Butterfly Yellow' in ray floret color as ray florets of plants of 'Butterfly Yellow' are lighter yellow in color.

BRIEF DESCRIPTION OF THE PHOTOGRAPHS

The accompanying photographs illustrate the overall appearance of the new *Argyranthemum* showing the colors as true as it is reasonably possible to obtain in colored reproductions of this type. Colors in the photographs may differ slightly from the color values cited in the detailed botanical description which accurately describe the colors of the new *Argyranthemum* plant.

The photograph at the bottom of the sheet comprises a side perspective view of a typical flowering plant of 'G15101' grown in a container.

The photograph at the top of sheet is a close-up view of a typical flowering plant of 'G15101'.

DETAILED BOTANICAL DESCRIPTION

The aforementioned photographs and following observations and measurements describe plants grown during the spring in 11.5-cm containers in an acrylic-covered greenhouse in Carleton, Mich. and under cultural practices typical of commercial potted *Argyranthemum* production. During the production of the plants, day and night temperatures ranged from 18° C. to 27° C. Plants were eleven weeks old when the photographs and description were taken. In the following description, color references are made to The Royal Horticultural Society Colour Chart, 2007 Edition, except where general terms of ordinary dictionary significance are used.

Botanical classification: *Argyranthemum frutescens* 'G15101'.

Parentage: Naturally-occurring whole plant mutation of *Argyranthemum frutescens* 'Butterfly', not patented.

Propagation:

*Type*.—Terminal vegetative cuttings.

*Time to initiate roots, summer*.—About one to two weeks at soil temperatures about 22° C.

*Time to initiate roots, winter*.—About two to three weeks at soil temperatures about 22° C.

*Time to produce a rooted young plant, summer*.—About three to four weeks at ambient temperatures about 22° C. to 27° C.

*Time to produce a rooted young plant, winter*.—About four to five weeks at ambient temperatures about 18° C. to 23° C.

*Root description*.—Medium in thickness, fibrous; close to white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Herbaceous perennial; upright to somewhat outwardly spreading plant habit; vigorous growth habit and moderate growth rate.

*Branching habit*.—Freely branching growth habit with about ten primary branches, each with about four to five secondary lateral branches developing per plant.

*Plant height, soil level to top of foliar plane*.—About 27 cm.

*Plant height, soil level to top of floral plane*.—About 38 cm.

*Plant width*.—About 43 cm.

*Lateral branches*.—Length: About 30 cm. Diameter: About 5 mm. Internode length: About 2.2 cm. Strength: Strong; young stems, flexible. Aspect: Highly variable, about 15° to about 45° from vertical. Texture: Smooth, glabrous. Luster: Matte. Color, developing: Close to 146C; at the internodes, close to 146C. Color, developed: Close to 146B; at the internodes, close to 146C.

Leaf description:

*Arrangement*.—Alternate, simple.

*Length*.—About 5.8 cm.

*Width*.—About 5 cm.

*Lobe depth*.—About 2.7 cm.

*Shape*.—Pinnatifid; in outline, elliptical.

*Apex*.—Acute.

*Base*.—Attenuate, equilateral.

*Margin*.—Deeply dissected with three to seven narrow lobes.

*Sinuses*.—Parallel.

*Texture, upper and lower surfaces*.—Smooth, glabrous.

*Luster, upper and lower surfaces*.—Matte.

*Venation*.—Pinnate.

*Color*.—Developing leaves, upper and lower surfaces: Close to 146A. Fully expanded leaves, upper surface: Close to 137B; venation, close to 146B. Fully expanded leaves, lower surface: Close to 146A; venation, close to 146B.

*Petioles*.—Length: About 3.4 cm. Diameter, flattened: About 5 mm. Strength: Moderately strong. Texture, upper and lower surfaces: Smooth, glabrous. Luster, upper and lower surfaces: Slightly glossy. Color, upper and lower surfaces: Close to 146B.

Inflorescence description:

*Inflorescence form and arrangement*.—Single-type terminal and axillary inflorescences held above and beyond the foliar plane on strong peduncles; ray and disc florets arranged acropetally on a receptacle; inflorescences face mostly upright to somewhat outwardly.

*Flowering habit*.—Freely flowering habit with about 132 inflorescence buds and open inflorescences per plant.

*Flowering season*.—Plants flower from spring to frost in Pennsylvania; flowering continuous during this period; plants begin flowering about six weeks after planting.

*Inflorescence longevity*.—Inflorescences last about five to seven days on the plant; inflorescences persistent.

*Fragrance*.—Moderately fragrant, sour.

*Inflorescence buds*.—Height: About 1.8 cm. Diameter: About 1.2 cm. Shape: Spherical to slightly conical.

Texture: Smooth, glabrous. Luster: Involucral bracts, slightly glossy; ray florets, matte. Color: Close to 7C.

*Inflorescence size*.—Diameter: About 5.3 cm. Depth (height): About 1.8 cm. Diameter of disc: About 1.5 cm. Receptacle diameter: About 1.7 cm. Receptacle height: About 5 mm. Receptacle shape: Flat and shallow dome. Receptacle color: Close to 146A, 146B to 146C.

*Ray florets*.—Quantity per inflorescence and arrangement: About 20 arranged in about 1 to 1.25 whorls. Length: About 2.6 cm. Width: About 6 mm. Shape: Ligulate. Apex: Rounded or minutely tri-dentate. Base: Attenuate. Margin: Entire. Aspect: Slightly upward; apices slightly recurved. Texture, upper and lower surfaces: Smooth, glabrous; shallow longitudinal ridges. Luster, upper and lower surfaces: Matte. Color: When opening and fully opened, upper surface: Close to 9A; venation, close to 9A; color becoming closer to 9B with development. When opening and fully opened, lower surface: Close to 9C; venation, close to 9C; color becoming closer to 9D with development.

*Disc florets*.—Quantity per inflorescence and arrangement: About 270 spirally arranged in about 14 whorls at the center of the receptacle. Length: About 6 mm. Diameter: About 1 mm. Shape: Tubular with five free apical lobes. Apex: Acute. Texture, inner and outer surfaces: Smooth, glabrous. Luster, inner and outer surfaces: Slightly glossy. Color, immature, inner and outer surfaces: Close to 17A. Color, immature, inner and outer surfaces: Close to 17A; venation, close to 17A; color does not change with development.

*Phyllaries*.—Quantity per inflorescence and arrangement: About 25 arranged in about three whorls. Length: About 8 mm. Width: About 3 mm. Shape: Elliptical. Apex: Acute. Base: Truncate. Margin: Entire. Texture, upper and lower surfaces: Smooth, glabrous; edges, membraneous. Luster, upper surface: Moderately glossy. Luster, lower surface: Matte. Color, upper surface: Close to 146B. Color, lower surface: Close to 146A to 146B.

*Peduncles*.—Length, terminal peduncle: About 7.2 cm. Diameter, terminal peduncle: About 2 mm. Length, third peduncle: About 8.7 cm. Diameter, third peduncle: About 2 mm. Angle: Terminal peduncle, curling upright; lateral peduncles, about 45° to 55° from primary lateral axis. Strength: Moderately strong. Texture: Smooth with shallow longitudinal ridges, glabrous. Luster: Matte. Color: Close to 146B.

*Reproductive organs*.—Androecium: No stamens observed to date. Gynoecium: Present on both ray and disc florets; one per floret. Pistil length: About 6 mm. Stigma diameter: About 1 mm. Stigma shape: Bi-parted. Stigma color: Close to 17A. Style length: About 2.5 mm. Style color: Close to 2B. Ovary color: Close to 157A.

*Seeds and fruits*.—Seed and fruit production has not been observed on plants of the new *Argyranthemum* to date.

Disease & pest resistance: Plants of the new *Argyranthemum* have not been shown to be resistant to pathogens and pests common to *Argyranthemum* plants.

Garden performance: Plants of the new *Argyranthemum* have been observed to have good garden performance and to tolerate rain, wind and to tolerate low temperatures about 1.7° C. and to be suitable for USDA Hardiness Zones 10 and 11.

It is claimed:

1. A new and distinct *Argyranthemum* plant named 'G15101' as illustrated and described.

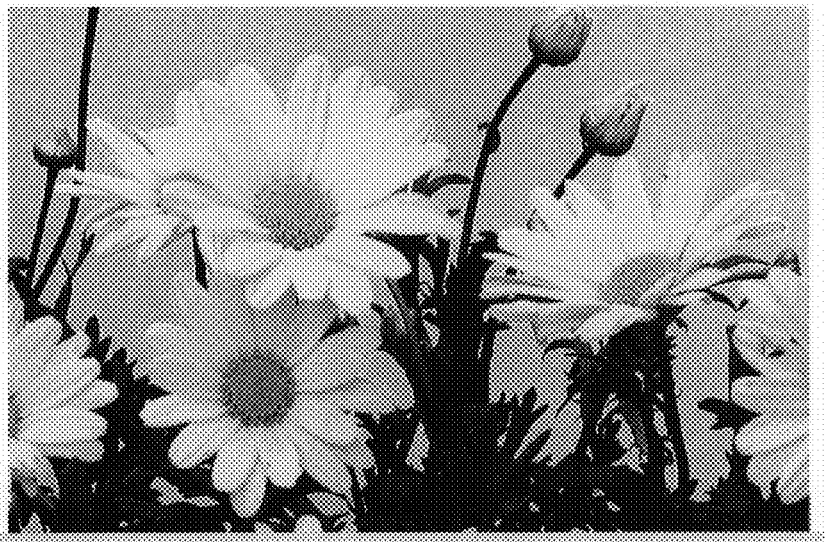
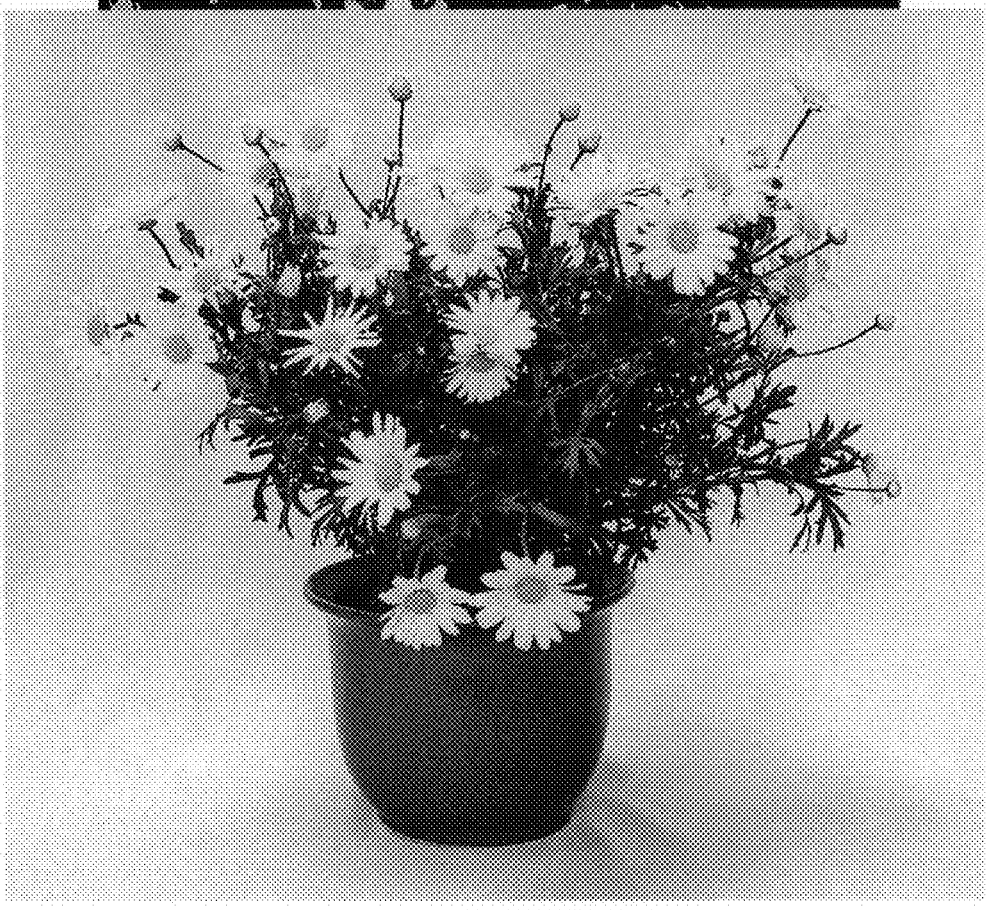

* * * * *